US006489110B1

(12) United States Patent
Oudshoorn et al.

(10) Patent No.: US 6,489,110 B1

(45) Date of Patent: Dec. 3, 2002

(54) EF-TU MRNA AS A MARKER FOR VIABILITY OF BACTERIA

(75) Inventors: Pieter Oudshoorn, St. Michielsgestel (NL); Paul R. Klatser, Amsterdam (NL)

(73) Assignee: bioMérieux, B.V. (NL)

( * ) Notice: Subject to any disclaimer, the term of this patent is extended or adjusted under 35 U.S.C. 154(b) by 0 days.

(21) Appl. No.: 09/600,770

(22) PCT Filed: Jan. 19, 1999

(86) PCT No.: PCT/EP99/00323

§ 371 (c)(1), (2), (4) Date: Jul. 21, 2000

(87) PCT Pub. No.: WO99/37804

PCT Pub. Date: Jul. 29, 1999

(30) Foreign Application Priority Data

Jan. 23, 1998 (EP) .......................................... 98200184

(51) Int. Cl.[7] .......................... C12Q 1/68; C12P 19/34; C07H 21/02; C07H 21/04

(52) U.S. Cl. ......................... 435/6; 435/91.1; 435/91.2; 536/23.1; 536/24.3; 536/24.31; 536/24.33

(58) Field of Search .......................... 435/6, 91.1, 91.2; 536/231, 24.3, 24.31, 24.33

(56) References Cited

U.S. PATENT DOCUMENTS 5,130,238 A * 7/1992 Malek et al. ................. 435/91
5,994,066 A 11/1999 Bergeron et al. .............. 435/6

FOREIGN PATENT DOCUMENTS

| | | |
|---|---|---|
| EP | 0 133 288 A2 | 7/1984 |
| WO | WO 96/06191 | 2/1996 |
| WO | WO 98/01559 | 1/1998 |
| WO | WO 98/18958 | 5/1998 |

OTHER PUBLICATIONS

DiCesare et al, "A High sensitivity electrochemiluminescence based detection system for automated PCR product quantitation", Biotechniques 15:152–156, Jun. 1993.*

Silbaq et al, "Nucleotide Sequence of *mycobacterium leprae* elongation factor (EF–Tu) gene", Nucleic Acids Res. 21(14):3327, Aug. 1993.*

An et al, "The nucleotide sequecne of tufB and four nearby tRNA structural genes of *Escherichia coli*", Gene 12:33–39, 1980.*

Carlin et al, "Monoclonal antibodies specfic for elongation factor TU and complete nucleotide sequecne of the tuf gene in *Mycobacterium tuberculosis*", Infection and Immunity 60(8):3136–3142, Jun. 1993.*

Berg Et Al., "Development of an Amplification and Hybridization Assay for the Specific and Sensitive Detection of Mycoplasma Fermentans DNA" Molecular and Cellular Probes, 1996, vol. 10, pp. 7–14.

Luneberg Et Al., "Detection of *Mycoplasma Pneumoniae* by Polymerase Chain Reaction and Nonradioactive Hybridization in Microtiter Plates," Journal of Clinical Microbiology, 1993, vol. 31, No. 5, pp. 1088–1094.

Vliet Et Al., "Assessment of Mycobacterial Viability by RNA Amplification," Antimicrobial Agents and Chemotherapy, 1994, vol. 38, No. 9, pp. 1959–1965.

Jou Et Al., "Single–Tube, Nested, Reverse Transcriptase PCR for Detection of Viable *Mycobacterium Tuberculosis*," Journal of Clinical Microbiology, 1997, vol. 35, No. 5, pp. 1161–1165.

Moore Et Al., "Amplification of rRNA for Assessment of Treatment Response of Pulmonary Tuberculosis Patients During Antimicrobial Therapy," Journal of Clinical Microbiology, 1996, vol. 34, No. 7, pp. 1745–1749.

Vaitilingom Et Al., "Direct Detection of Viable Bacteria, Molds, and Yeasts by Reverse Transcriptasa PCR in Contaminated Milk Samples after Heat Treatment," Applied and Environmental Microbiology, 1998, vol. 64. No. 3, pp. 1157–1160.

* cited by examiner

*Primary Examiner*—Jeffrey Fredman
(74) *Attorney, Agent, or Firm*—Myers Bigel Sibley & Sajovec

(57) ABSTRACT

The present invention is related to the detection of bacteria, such as Mycobacteria, in human or animal body fluids such as blood, sputum and urine. The present invention provides a method for assessing the viability of bacteria such as *Mycobacterium tuberculosis* without the need for propagation of the bacteria. The method of the present invention is in particular useful for assessing the viability of Mycobacteria species such as are *M. tuberculosis* or *M. leprae.* With the present invention oligonucleotides are provided that can be used as primers and probes for the amplification of bacterial EF-Tu mRNA. The use of the oligonucleotides according to the invention is not limited to any particular amplification technique or any particular modification thereof. It is evident that the oligonucleotides according to the invention find their use in many different nucleic aid amplification techniques and various methods for detecting the presence of (amplified) bacterial EF-Tu mRNA.

9 Claims, 5 Drawing Sheets

Figure 1a: The analytical sensitivity of NASBA using in vitro produced myuobacterial EF-Tu RNA
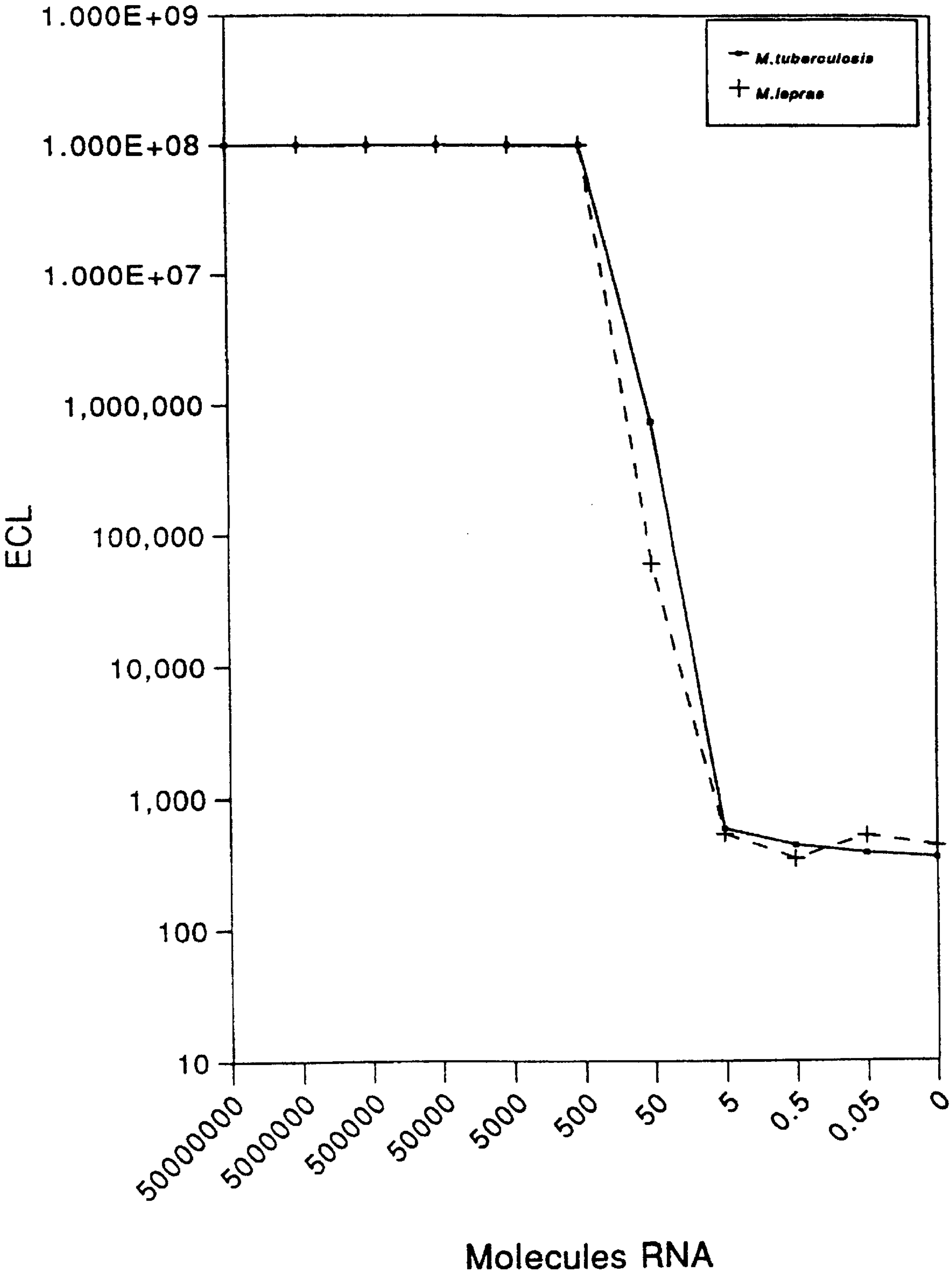

Figure 1b: The analytical sensitivity of NASBA using in vitro produced *E.coli* EF-Tu RNA
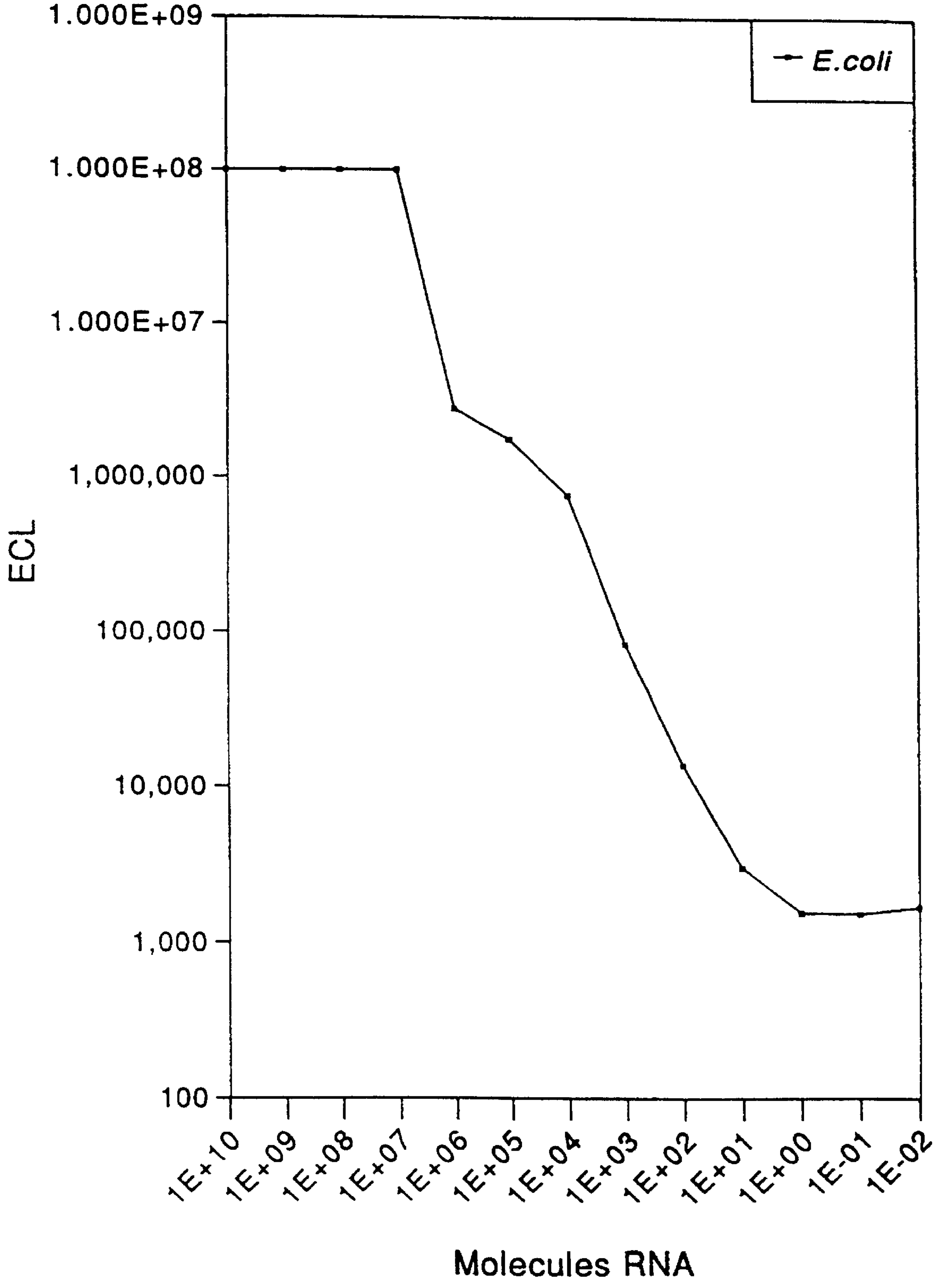

Figure 2: Specificity of the M. tuberculosis NASBA
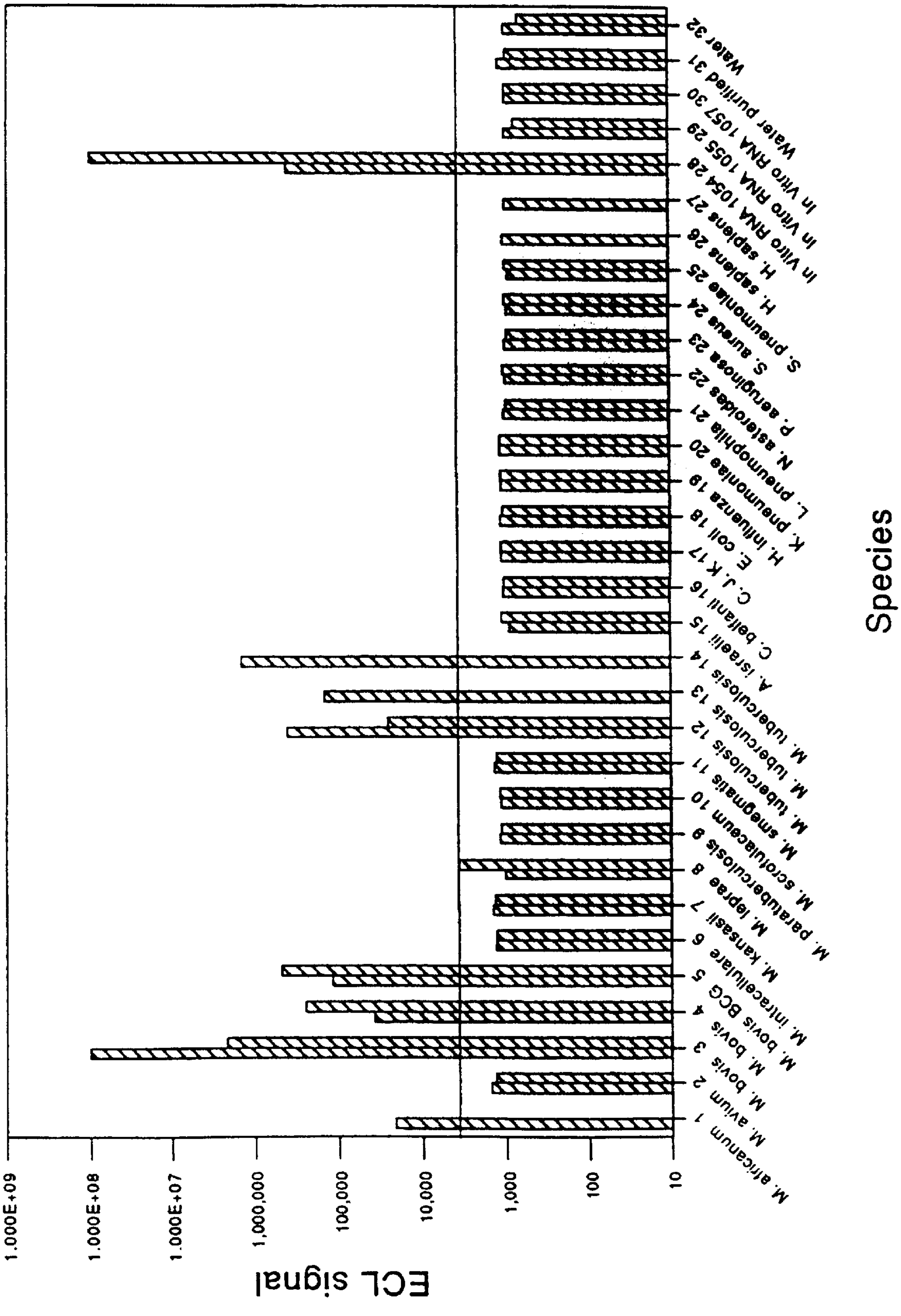

Figure 3: Specificity of the M. leprae NASBA
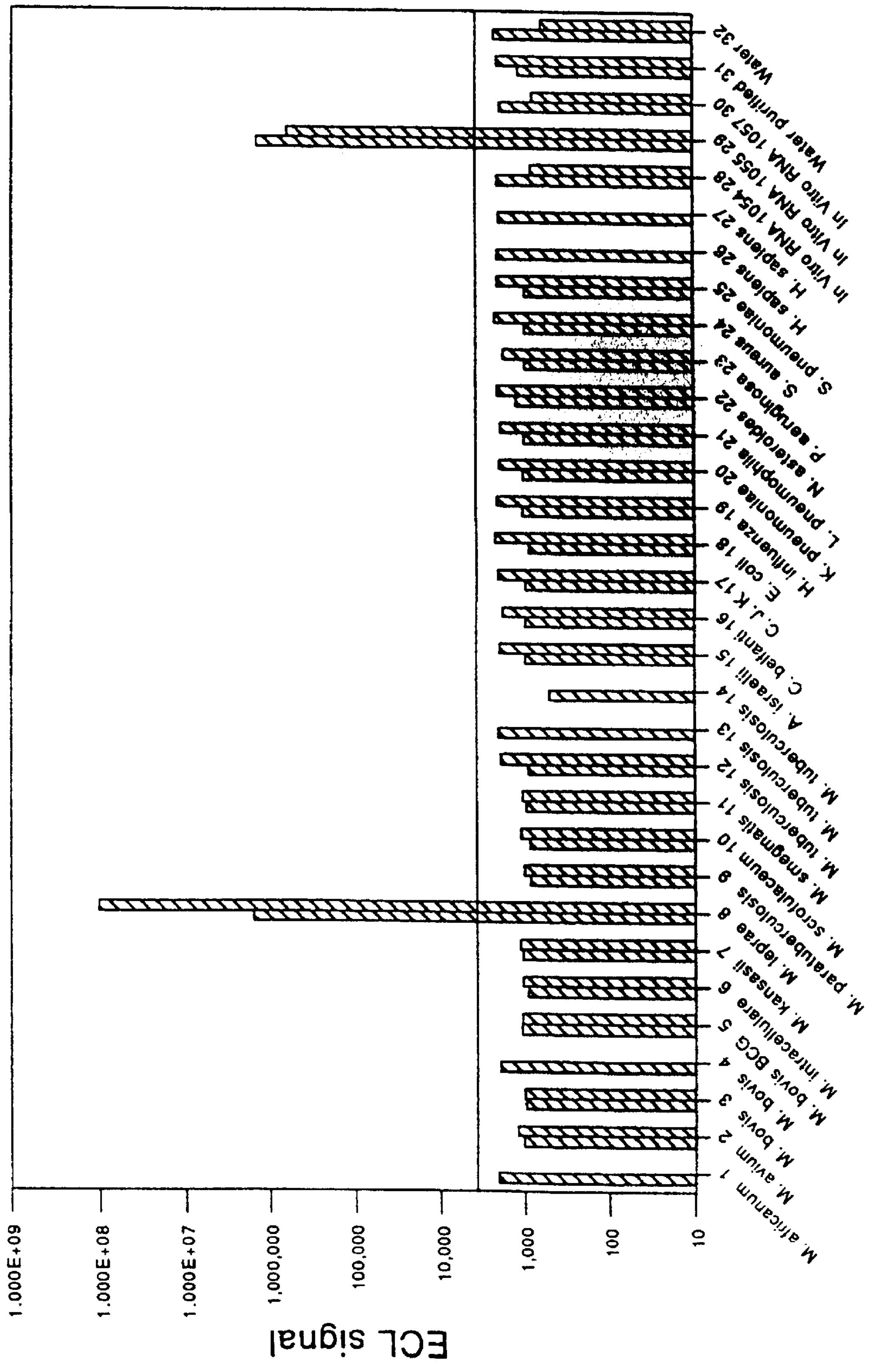

Figure 4: NASBA for viability assessment
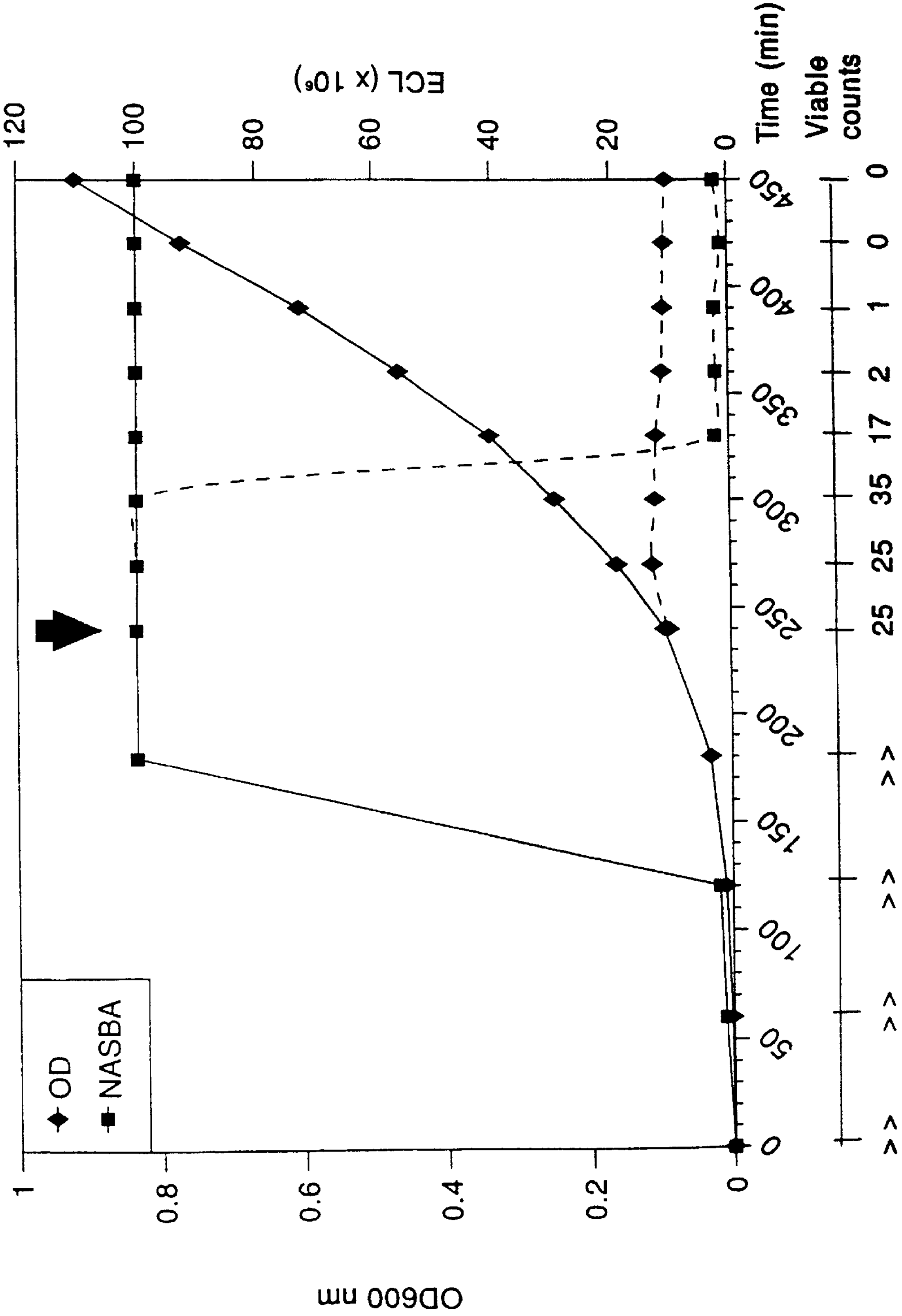

SEQUENCE LISTING

```
<160> NUMBER OF SEQ ID NOS: 95

<210> SEQ ID NO 1
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: Oligonucleotide primer to Mycobacterium
      tuberculosis EF-Tu.

<400> SEQUENCE: 1

aattctaata cgactcacta tagggagagc ttggtggtcg atgggcga              48


<210> SEQ ID NO 2
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Oligonucleotide primer to Mycobacterium
      tuberculosis EF-Tu.

<400> SEQUENCE: 2

cctctgtcga ggaactgatg a                                            21


<210> SEQ ID NO 3
<211> LENGTH: 49
<212> TYPE: DNA
<213> ORGANISM: Artificial Sequence
<220> FEATURE:
<221> NAME/KEY: misc_feature
<222> LOCATION: (1)..(49)
<223> OTHER INFORMATION: Oligonucleotide primer to Mycobacterium leprae
      EF-Tu.

<400> SEQUENCE: 3

aattctaata cgactcacta tagggagagg gtcgtctgac gaatgccga             49


<210> SEQ ID NO 4
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Oligonucleotide primer to Mycobacterium leprae
      EF-Tu.

<400> SEQUENCE: 4
```

-continued agtctgtcac acagttgatg g 21

<210> SEQ ID NO 5
<211> LENGTH: 49
<212> TYPE: DNA
<213> ORGANISM: Artificial Sequence
<220> FEATURE:
<221> NAME/KEY: misc_feature
<222> LOCATION: (1)..(49)
<223> OTHER INFORMATION: Oligonucleotide primer to Escherichia coli EF-Tu.

<400> SEQUENCE: 5
aattctaata cgactcacta tagggagagc tgagtctctt tgataccaa 49

<210> SEQ ID NO 6
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Oligonucleotide primer to Escherichia coli EF-Tu.

<400> SEQUENCE: 6
cgaaaatcct ggaactggct g 21

<210> SEQ ID NO 7
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic oligonucleotide to Mycobacterium leprae and M. tubercul o

<400> SEQUENCE: 7
gcgcggcgtg gtcaacgt 18

<210> SEQ ID NO 8
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic oligonucleotide to Mycobacterium leprae and M. tubercul o

<400> SEQUENCE: 8
acgaggaagt tgagatcg 18

<210> SEQ ID NO 9
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic oligonucleotide.

<400> SEQUENCE: 9
cttggtggtc gatgggcga 19

<210> SEQ ID NO 10
<211> LENGTH: 20

-continued

<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide.

<400> SEQUENCE: 10
ggtcgtctga cgaatgccga 20

<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide.

<400> SEQUENCE: 11
ctgagtctct ttgataccaa 20

<210> SEQ ID NO 12
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Oligonucleotide primer to Escherichia coli.

<400> SEQUENCE: 12
acgcggtatc atcaaagt 18

<210> SEQ ID NO 13
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Oligonucleotide primer to Escherichia coli.

<400> SEQUENCE: 13
gtgaagaagt tgaaatcg 18

<210> SEQ ID NO 14
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic oligonucleotide.

<400> SEQUENCE: 14
gtcggaagta gaactgcg 18

<210> SEQ ID NO 15
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic oligonucleotide.

<400> SEQUENCE: 15

-continued

```
gaccccggca cgccgact                                                    18


<210> SEQ ID NO 16
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic oligonucleotide.

<400> SEQUENCE: 16

gacaagccgt tcctgtgcc                                                   19


<210> SEQ ID NO 17
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic oligonucleotide.

<400> SEQUENCE: 17

gtcggaagta gaactgcg                                                    18


<210> SEQ ID NO 18
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic oligonucleotide.

<400> SEQUENCE: 18

ggcacaggaa cggcttgtc                                                   19


<210> SEQ ID NO 19
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide.

<400> SEQUENCE: 19

ggcatcagga acggcttgtc                                                  20


<210> SEQ ID NO 20
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide to Mycobacterium
      tuberculosis complex EF

<400> SEQUENCE: 20

agtgggtgtg ccctacatcc tggtagcgct g                                     31


<210> SEQ ID NO 21
<211> LENGTH: 31
<212> TYPE: DNA
<213> ORGANISM: Artificial Sequence
<220> FEATURE:
```

-continued

```
<221> NAME/KEY: misc_feature
<222> LOCATION: (1)..(31)
<223> OTHER INFORMATION: Synthetic oligonucleotide to Mycobacterium
      laprae EF-Tu.

<400> SEQUENCE: 21

ggtgggtgta ccttacatcc tggtcgcact t                              31


<210> SEQ ID NO 22
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide Mycobacterium avium
      and M. paratubercul o

<400> SEQUENCE: 22

ggtcggtgtg ccctacatcc tggtcgcgct g                              31


<210> SEQ ID NO 23
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide Micrococcus luteus
      EF-Tu.

<400> SEQUENCE: 23

ggtcggcgtg ccggccctgc tcgtggccct g                              31


<210> SEQ ID NO 24
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide to Streptomyces
      coelicolor EF-Tu.

<400> SEQUENCE: 24

ggtcggcgtt ccgtacatcg tggtcgccct g                              31


<210> SEQ ID NO 25
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide to Corynebacterium
      glutamicum EF-Tu.

<400> SEQUENCE: 25

ggttggcgtt ccttacatcc tcgttgctct t                              31


<210> SEQ ID NO 26
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide to Corynebacterium
      J.K EF-Tu.
```

-continued

<400> SEQUENCE: 26
ggttggcgtt ccttacatcc tggttgcact g 31

<210> SEQ ID NO 27
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide to E. coli, Nocardia asteroides, and Kl e

<400> SEQUENCE: 27
ggtaggcgtt ccgtacatca tcgtgttcct g 31

<210> SEQ ID NO 28
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic oligonucleotide to Pseudomonas aeruginosa EF-Tu.

<400> SEQUENCE: 28
ggtaggcgtt ccctacatcg tcgtgttcct g 31

<210> SEQ ID NO 29
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Mycobacterium tuberculosis complex an

<400> SEQUENCE: 29
ctgcccagga attcgacgag 20

<210> SEQ ID NO 30
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Mycobacterium avium and M. paratuber c

<400> SEQUENCE: 30
ccgcccagga gttcgacgag 20

<210> SEQ ID NO 31
<211> LENGTH: 14
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Synthetic oligonucleotide to Mycobacterium intracellulare EF-Tu.

<400> SEQUENCE: 31
ccgcccagga gttc 14

-continued

```
<210> SEQ ID NO 32
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic oligonucleotide to Escherichia coli
      EF-Tu.

<400> SEQUENCE: 32

tctcagtacg acttcccggg c                                               21


<210> SEQ ID NO 33
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic oligonucleotide to Nocardia
      asteroides and Klebsiella p n

<400> SEQUENCE: 33

tctcagtacg atttcccggg c                                               21


<210> SEQ ID NO 34
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Micrococcus luteus
      EF-Tu.

<400> SEQUENCE: 34

cctccaggag cttcgacgtc                                                 20


<210> SEQ ID NO 35
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic oligonucleotide to Streptomyces
      coelicolor EF-Tu.

<400> SEQUENCE: 35

ctccgagtac gagttcccgg gcgac                                           25


<210> SEQ ID NO 36
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic oligonucleotide to Corynebacterium
      glutamicum EF-Tu.

<400> SEQUENCE: 36

ctgagcagga ctacgac                                                    17


<210> SEQ ID NO 37
<211> LENGTH: 21
```

-continued

<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic oligonucleotide to Pseudomonas aeruginosa EF-Tu.

<400> SEQUENCE: 37
aacacctacg acttcccggg c 21

<210> SEQ ID NO 38
<211> LENGTH: 4
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: Synthetic oligonucleotide to Mycobacterium tuberculosis complex, M

<400> SEQUENCE: 38 gctc 4

<210> SEQ ID NO 39
<211> LENGTH: 4
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: Synthetic oligonucleotide to Mycobacterium leprae EF-Tu.

<400> SEQUENCE: 39 attg 4

<210> SEQ ID NO 40
<211> LENGTH: 4
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: Synthetic oligonucleotide to Micrococcus luteus, Streptomyces coe l

<400> SEQUENCE: 40 tctg 4

<210> SEQ ID NO 41
<211> LENGTH: 4
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: Synthetic oligonucleotide to Pseudomonas aeruginosa EF-Tu.

<400> SEQUENCE: 41 gctg 4

<210> SEQ ID NO 42
<211> LENGTH: 23
<212> TYPE: DNA
<213> ORGANISM: Artificial Sequence
<220> FEATURE:
<221> NAME/KEY: misc_feature -continued

```
<222> LOCATION: (1)..(23)
<223> OTHER INFORMATION: Synthetic oligonucleotide to Mycobacterium
      tuberculosis complex EF

<400> SEQUENCE: 42

ttgctctgtc gaggaactga tga                                          23


<210> SEQ ID NO 43
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Mycobacterium
      tuberculosis (AC X63539

<400> SEQUENCE: 43

ttgcctctgt cgaggaactg atga                                         24


<210> SEQ ID NO 44
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Mycobacterium
      leprae EF-Tu.

<400> SEQUENCE: 44

tcgagtctgt cacacagttg atgg                                         24


<210> SEQ ID NO 45
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Micrococcus luteus
      EF-Tu.

<400> SEQUENCE: 45

tcaagtccgt cgaggacctc atgg                                         24


<210> SEQ ID NO 46
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Streptomyces
      coelicolor EF-Tu.

<400> SEQUENCE: 46

gcaactcggt cctcgagctc atga                                         24


<210> SEQ ID NO 47
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Corynebacterium
      glutamicum EF-Tu.
```

-continued

<400> SEQUENCE: 47
gcaagcagat ccttgagctc atgc 24

<210> SEQ ID NO 48
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic oligonucleotide to Mycobacterium avium and M. paratuber c

<400> SEQUENCE: 48
tggagtccgt cgagcag 17

<210> SEQ ID NO 49
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Escherichia coli EF-Tu.

<400> SEQUENCE: 49
aagcgaaaat cctggaactg gctggc 26

<210> SEQ ID NO 50
<211> LENGTH: 11
<212> TYPE: DNA
<213> ORGANISM: Artificial Sequence
<220> FEATURE:
<221> NAME/KEY: misc_feature
<222> LOCATION: (1)..(11)
<223> OTHER INFORMATION: Synthetic oligonucleotide to Nocardia asteroides and Klebsiella p n

<400> SEQUENCE: 50
aagcgaaaat c 11

<210> SEQ ID NO 51
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic oligonucleotide to Mycobacterium tuberculosis EF-Tu.

<400> SEQUENCE: 51
cattaccggc cgcgga 16

<210> SEQ ID NO 52
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic oligonucleotide to Mycobacterium leprae EF-Tu.

<400> SEQUENCE: 52
tatcaccggt cgtggc 16

-continued

<210> SEQ ID NO 53
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium tuberculosis complex EF

<400> SEQUENCE: 53
tcggcattcg cccatcgacc accaag 26

<210> SEQ ID NO 54
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium leprae EF-Tu.

<400> SEQUENCE: 54
tcggcattcg tcagacgacc accaag 26

<210> SEQ ID NO 55
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium intracellulare EF-Tu.

<400> SEQUENCE: 55
tcggcatccg cccgaccagc accaag 26

<210> SEQ ID NO 56
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium avium and M. paratuber c

<400> SEQUENCE: 56
tcggcatccg cccgtccagc accaag 26

<210> SEQ ID NO 57
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium smegmatis EF-Tu.

<400> SEQUENCE: 57
tcggcatccg cccggagacc accaag 26

<210> SEQ ID NO 58
<211> LENGTH: 24
<212> TYPE: DNA

-continued

<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Escherichia coli EF-Tu.

<400> SEQUENCE: 58
ttggtatcaa agagactcag aagt 24

<210> SEQ ID NO 59
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Klebsiella pneumoniae EF-Tu.

<400> SEQUENCE: 59
ttggtatcaa agagaccgcg aaaa 24

<210> SEQ ID NO 60
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Pseudomonas aeruginosa EF-Tu.

<400> SEQUENCE: 60
tcggcatcaa ggcgaccacc aaga 24

<210> SEQ ID NO 61
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic oligonucleotide to Mycobacterium scrofulaceum EF-Tu.

<400> SEQUENCE: 61
cattaagccg cccagcacca aga 23

<210> SEQ ID NO 62
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium kansasii EF-Tu.

<400> SEQUENCE: 62
tcggcatccg tccgacacca ccaaga 26

<210> SEQ ID NO 63
<211> LENGTH: 20
<212> TYPE: DNA
<213> ORGANISM: Artificial Sequence
<220> FEATURE:
<221> NAME/KEY: misc_feature
<222> LOCATION: (1)..(20)

-continued

<223> OTHER INFORMATION: Synthetic oligonucleotide to Mycobacterium
tuberculosis complex EF

<400> SEQUENCE: 63
tggtttgctg ctgcggggcg 20

<210> SEQ ID NO 64
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Mycobacterium
leprae EF-Tu.

<400> SEQUENCE: 64
tggtctgttg ttgcgtggca 20

<210> SEQ ID NO 65
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Mycobacterium
intracellulare, M. avi u

<400> SEQUENCE: 65
cggtctgctg ctgcgtggta 20

<210> SEQ ID NO 66
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic oligonucleotide to Pseudomonas
aeruginosa EF-Tu.

<400> SEQUENCE: 66
tggtaacctg ctgcgctggc a 21

<210> SEQ ID NO 67
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Mycobacterium
scrofulaceum EF-Tu.

<400> SEQUENCE: 67
cggtctgttg ctccgtggca 20

<210> SEQ ID NO 68
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic oligonucleotide to Mycobacterium
kansasii EF-Tu.

<400> SEQUENCE: 68

-continued cgggtctgtt tgctgcgtgg tg 22

<210> SEQ ID NO 69
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Escherichia coli EF-Tu.

<400> SEQUENCE: 69
aggtgttctg ctgcgcggta 20

<210> SEQ ID NO 70
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Klebsiella pneumoniae EF-Tu.

<400> SEQUENCE: 70
aggtgttctg ctgcgtggta 20

<210> SEQ ID NO 71
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Mycobacterium tuberculosis EF-Tu.

<400> SEQUENCE: 71
ttgcctctgt cgaggaactg atga 24

<210> SEQ ID NO 72
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Mycobacterium leprae EF-Tu.

<400> SEQUENCE: 72
tcgagtctgt cacacagttg atgg 24

<210> SEQ ID NO 73
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Micrococcus luteus EF-Tu.

<400> SEQUENCE: 73
tcaagtccgt cgaggacctc atgg 24

-continued

<210> SEQ ID NO 74
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Streptomyces coelicolor EF-Tu.

<400> SEQUENCE: 74
gcaactcggt cctcgagctc atga 24

<210> SEQ ID NO 75
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Corynebacterium glutamicum EF-Tu.

<400> SEQUENCE: 75
gcaagcagat ccttgagctc atgc 24

<210> SEQ ID NO 76
<211> LENGTH: 14
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Synthetic oligonucleotide to Mycobacterium leprae EF-Tu.

<400> SEQUENCE: 76
tcgagtctgt caac 14

<210> SEQ ID NO 77
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic oligonucleotide to Mycobacterium tuberculosis H37Rv, M.

<400> SEQUENCE: 77
ttgctctgtc gaggaactga t 21

<210> SEQ ID NO 78
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic oligonucleotide to Mycobacterium avium EF-Tu.

<400> SEQUENCE: 78
tggagtccgt cgagcagctg at 22

<210> SEQ ID NO 79
<211> LENGTH: 17
<212> TYPE: DNA
<213> ORGANISM: Artificial Sequence -continued

```
<220> FEATURE:
<221> NAME/KEY: misc_feature
<222> LOCATION: (1)..(17)
<223> OTHER INFORMATION: Synthetic oligonucleotide to Mycobacterium
      paratuberculosis EF-Tu.

<400> SEQUENCE: 79

tggagtccgt cgagcag                                                    17


<210> SEQ ID NO 80
<211> LENGTH: 14
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Synthetic oligonucleotide to Mycobacterium
      tuberculosis EF-Tu.

<400> SEQUENCE: 80

ttgctctgtc gagg                                                       14


<210> SEQ ID NO 81
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Escherichia coli
      EF-Tu.

<400> SEQUENCE: 81

aagcgaaaat cctggaactg gctggc                                          26


<210> SEQ ID NO 82
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide to Escherichia coli
      EF-Tu.

<400> SEQUENCE: 82

aagcgaaaat cctggaactg                                                 20


<210> SEQ ID NO 83
<211> LENGTH: 11
<212> TYPE: DNA
<213> ORGANISM: Artificial Sequence
<220> FEATURE:
<221> NAME/KEY: misc_feature
<222> LOCATION: (1)..(11)
<223> OTHER INFORMATION: Synthetic oligonucleotide to Nocardia
      asteroides EF-Tu.

<400> SEQUENCE: 83

aagcgaaaat c                                                          11


<210> SEQ ID NO 84
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium
```

-continued leprae EF-Tu.

<400> SEQUENCE: 84
tcggcattcg tcagacgacc accaag 26

<210> SEQ ID NO 85
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium tuberculosis and M. bo v

<400> SEQUENCE: 85
tcggcattcg cccatcgacc accaag 26

<210> SEQ ID NO 86
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium leprae EF-Tu.

<400> SEQUENCE: 86
tcggcattcg tcagacgacc accaag 26

<210> SEQ ID NO 87
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium intracellulare EF-Tu.

<400> SEQUENCE: 87
tcggcatccg cccgaccagc accaag 26

<210> SEQ ID NO 88
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacteriu m bovis BCG, M. tubercul o

<400> SEQUENCE: 88
tcggcattcg cccatcgacc accaag 26

<210> SEQ ID NO 89
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium avium and M. paratuber c

<400> SEQUENCE: 89

-continued tcggcatccg cccgtccagc accaag 26

<210> SEQ ID NO 90
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium smegmatis EF-Tu.

<400> SEQUENCE: 90
tcggcatccg cccggagacc accaag 26

<210> SEQ ID NO 91
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic oligonucleotide to Mycobacterium scrofulaceum EF-Tu.

<400> SEQUENCE: 91
tcagcattaa gccgcccagc accaag 26

<210> SEQ ID NO 92
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic oligonucleotide to Mycobacterium kansasii EF-Tu.

<400> SEQUENCE: 92
tcggcatccg tccgacacca ccaag 25

<210> SEQ ID NO 93
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Escherichia coli EF-Tu.

<400> SEQUENCE: 93
ttggtatcaa agagactcag aagt 24

<210> SEQ ID NO 94
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Klebsiella pneumoniae EF-Tu.

<400> SEQUENCE: 94
ttggtatcaa agagaccgcg aaaa 24

<210> SEQ ID NO 95

-continued

```
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide to Pseudomonas
      aeruginosa EF-Tu.

<400> SEQUENCE: 95

tcggcatcaa ggcgaccacc aaga                                        24
```

EF-TU MRNA AS A MARKER FOR VIABILITY OF BACTERIA

The present invention is related to the detection of bacteria, such as Mycobacteria, in human or animal body fluids such as blood, sputum and urine. The present invention provides a method for assessing the viability of bacteria such as Mycobacterium tuberculosis without the need for propagation of the bacteria.

For example, tuberculosis (TB) caused by Mycobacterium tuberculosis is a major public health problem in many countries world-wide with particular significance in developing countries. Tuberculosis control programmes are faced with an increased burden of cases, a shift towards diagnostically more difficult categories of patients such as extrapulmonary and smear-negative cases, and the emergence of multidrug-resistant strains of *M. tuberculosis*. Improved diagnosis would be a valuable contribution in the struggle to solve this global public health emergency.

The method of the present invention is concerned with the amplification of specific nucleic acid sequences.

Nucleic acid amplification reactions promise to reduce the time for diagnosis from weeks to hours, while surpassing the sensitivity and specificity of the classical methods. Besides their potential value in diagnosis, amplification reactions offer the possibility of a rapid identification and drug-susceptibility determination. Amplification of DNA target molecules to a detectable level by the polymerase chain reaction (PCR) is the best analyzed system for detecting Mycobacteria.

The "Polymerase Chain Reaction" (PCR) is described in European patent applications EP 200362 and EP 201148. PCR is a cyclic process which has double stranded DNA as target. Each cycle in the PCR process starts with the separation of a double stranded DNA target in its two complementary strands. To each strand a primer will anneal and DNA polymerases present will extend the primers along the DNA strand to which it annealed thus forming two new DNA duplexes. When the reaction mixture is heated the strands of the DNA duplexes will be separated again and a new PCR cycle can start. Thus, the PCR process produces multiple DNA copies of a DNA target. Amplification using PCR, can also be based on an RNA template. The actual PCR needs to be preceded by a reverse transcription step to copy the RNA into DNA (RT-PCR). However, if RT-PCR is used for the detection of transcripts differentiation of mRNA- and DNA-derived PCR products is necessary. DNAse treatment prior to RT-PCR can be employed (Bitsch, A. et al., J Infect. Dis 167, 740–743., 1993; Meyer, T. et al., Mol. Cell Probes. 8, 261–271., 1994), but sometimes fails to remove contaminating DNA sufficiently [Bitsch, A. et al., 1993].

More recently a different class of nucleic acid amplification methods namely the "transcription based amplification techniques" was developed. The techniques involve the transcription of multiple RNA copies from a template comprising a promoter recognized by an RNA polymerase. Said copies are used as input for further amplification. Such methods have been described by Gingeras et al. in WO88/10315 and Burg et al. in WO89/1050. Isothermal transcription based amplification techniques have been described by Davey et al. in EP 323822 (relating to the NASBA method), by Gingeras et al. in EP 373960 and by Kacian et al. in EP 408295 (the TMA method). Transcription based amplification reactions may also be performed with thermostable enzymes. Such a thermostable method is described in EP 682121 filed in the name of Toyo Boseki KK.

The isothermal transcription based nucleic acid amplification techniques have been utilized to detect mycobacteria, such as the NASBA method [Vliet, G. M. E. van der, Schukkink, R. A. F., Gemen, B. van, Schepers, P. and Klatser, P. R. (1993) Nucleic acid sequence-based amplification (NASBA) for the identification of mycobacteria. J. Gen. Microbiol. 139, 2423–2429.] and another transcription-mediated RNA amplification test (TMA) [Jonas, V., Alden, M. J., Curry, J. I., Kamisango, K., Knott, C. A., Lankford, R., Wolfe, J. and Moore, D. F. (1993) Detection and identification of Mycobacterium tuberculosis directly from sputum sediments by amplification of rRNA. J. Clin. Microbiol. 31, 241] both targeted at 16S ribosomal RNA.

Amplification reactions targeted at the 16S rRNA or the gene encoding it are usually directed to a conserved region which comprises species-specific variable sequences [Vliet, G. M. E. van der, Schukkink, R. A. F., Gemen, B. van, Schepers, P. and Klatser, P. R. (1993) Nucleic acid sequence-based amplification (NASBA) for the identification of mycobacteria. J. Gen. Microbiol. 139, 2423–2429., Jonas, V., Alden, M. J., Curry, J. I., Kamisango, K., Knott, C. A., Lankford, R., Wolfe, J. and Moore, D. F. (1993) Detection and identification of Mycobacterium tuberculosis directly from sputum sediments by amplification of rRNA. J. Clin. Microbiol. 31, 241]. They have the advantage that a single amplification reaction can identify the mycobacterial species. An additional advantage of the transcription-mediated RNA amplification assays targeted at 16S rRNA, is the high number of target molecules per cell–±2000; sensitivity is thereby favoured.

Since RNA, especially mRNA, has a generally much shorter half-life time than DNA, its detection may be useful for the assessment of the viability of mycobacteria [Moore, D. F., Curry, J. I., Knott, C. A. and Jonas, V. (1996) Amplification of rRNA for assessment of treatment response of pulmonary tuberculosis patients during antimicrobial therapy. J. Clin. Microbiol. 34, 1745–1749., Vliet, G. M. E. van der, Schepers, P., Schukkink, R. A. F., Gemen, B. van and Klatser, P. R. (1994) Assessment of mycobacterial viability by RNA amplification. Antimicrob. Agents Chemother. 38, 1959–1965.], which is relevant to the problems of resistance against drugs and contagiousness of the patient.

The present invention is based on the detection of mRNA encoding the elongation factor EF-Tu.

The elongation factor EF-Tu is essential in (myco) bacterial translation. Elongation factors play an ancillary role in the elongation step of translation and are thus an indicator of the cell's metabolic activity. For every translation EF-Tu is required. The amount of EF-Tu protein can be as high as 50% of their total protein content in active proliferating cells.

EF-Tu encoding gene sequences (DNA) have been used as a marker to detect the presence of bacterial cells.

In EP133288 a method is disclosed for the detection of bacterial DNA with a probe comprising a base sequence of at least a portion of one of the strands of a tuf or fus gene. Southern blot hybridization of the digested mycoplasmal DNAs with the elongation factor (EF-Tu) gene tuf of *E.coli* was used as a basis to detect polymorphism in mycoplasma strains.[Yogev et al. FEMS Microbiol.Lett., 50(2–3), 145–9, 1988].

A PCR based assays for the detection of Mycoplasma tuberculosis, and Mycoplasma fermentans using the gene encoding elongation factor Tu (tuf) as the target sequence had also been described [Berg et al.,Mol.Cell.Probes, 10(1), 7–14, 1996 and Luneberg et al., J.Clin.Microbiol., 31(5), 1088–94, 1993].

The present invention, however, is concerned with the detection of EF-Tu mRNA as a marker for bacterial viability.

The present invention thus provides a method for the assessment of bacterial viability whereby mRNA coding for the elongation factor EF-Tu is used as a target in a nucleic acid amplification reaction and the presence and/or amount of said mRNA is determined.

The presumably short-lived mRNA coding for the EF-Tu is most likely highly abundant in the (myco)bacterial cell and a decrease therein will indicate a decline in metabolic activity. Furthermore, because of the EF-Tu's essential role, it is plausible to assume that it is present in all mycobacterial species, allowing the development of a general amplification system with species-specific primers and/or probes, analogous to the 16S rRNA NASBA design [Vliet, G. M. E. van der, Schukkink, R. A. F., Gemen, B. van, Schepers, P. and Klatser, P. R. (1993) Nucleic acid sequence-based amplification (NASBA) for the identification of mycobacteria. J. Gen. Microbiol. 139, 2423–24291.].

With the method of the present invention, preferably a transcription based amplification technique, such a NASBA, is used for the amplification of the bacterial EF-Tu mRNA. In contrast to RT-PCR, NASBA, which is based on RNA transcription by T7 RNA polymerase (Kievits et al., 1991; Compton, 1991), does not need differentiation between RNA- and DNA-derived amplification products since it uses RNA as its principal target.

The amplified products may be detected using a complementary labeled probe.

Numerous protocols have been described for the detection of amplified products [Klatser, P R. (1995) Amplification reactions in mycobacteriology. J. Microbiol. Meth. 23, 75–87.]. Preferably homogeneous assays are used, because they would allow amplification reaction mixtures to be sealed before amplification is initiated. One such system, electro-chemiluminescence (ECL), has already been succesfully applied to detect amplified products in NASBA [Gemen, B. van, Beuningen, R. van, Nabbe, A., Strijp, D. van, Jurriaans, S., Lens, P., Kievits, T. (1994) A one-tube quantitative HIV-I RNA NASBA nucleic acid amplification assay using electrochemiluminescent (ECL) labelled probes. J. Virol. Methods, 49, 157–167.].

The method of the present invention is in particular useful for assessing the viability of Mycobacteria species such as are *M. tuberculosis* or *M. leprae.*

With the present invention oligonucleotides are also provided that can be used as primers and probes for the amplification of bacterial EF-Tu mRNA.

The use of the oligonucleotides according to the invention is not limited to any particular amplification technique or any particular modification thereof. It is evident that the oligonucleotides according to the invention find their use in many different nucleic acid amplification techniques and various methods for detecting the presence of (amplified) bacterial EF-Tu mRNA. The oligonucleotides of the present invention can likewise be used in quantitative amplification methods. An example of such quantitative method is described in EP 525882.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone instead of the phosphate sugar backbone of normal nucleic acid) or the like. It is evident that these alternative structures, representing the sequences of the present invention are likewise part of the present invention.

The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary or homologous to the target sequence, but somewhat longer primers are preferred. Usually primers contain about 15–26 nucleotides but longer primers may also be employed, especially when the primers contain additional sequences such as a promoter sequence for a particular polymerase.

Normally a set of primers will consist of at least two primers, one 'upstream' and one 'downstream' primer which together define the amplificate (the sequence that will be amplified using said primers).

Primarily for the use in transcription based amplification techniques, the oligonucleotides according to the invention may also be linked to a promoter sequence. The term "promoter sequence" defines a region of a nucleic acid sequence that is specifically recognized by an RNA polymerase that binds to a recognized sequence and initiates the process of transcription by which an RNA transcript is produced. In principle any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Oligonucleotides linked to a promoter sequence are commonly referred to as "promoter primers".

Oligonucleotides according to the invention are substantially complementary to a sequence of a bacterial EF-Tu mRNA sequence, said oligonucleotide being 10–50 nucleotides in length and comprising at least 10 consecutive nucleotides of one of the sequences depicted in SEQ ID 1–8 or the complementary sequence thereof.

Oligonucleotides comprising (a part of) SEQ ID's 1 and 2 have proven to be suitable for the amplification of Ef-Tu mRNA sequences of *M. tuberculosis.* In the event amplification is carried out with a transcription based amplification technique one of said oligonucleotides may also comprise a promoter sequence. Of course, such "promoter-oligonucleotides" are likewise art of the invention. In the sequence as depicted in SEQ ID 9 the T7 promoter has been linked to the sequence as depicted in SEQ ID 1. In the experimental part of this application these sequences are indicated as TUF15 (SEQ ID 9) and TUF 18 (SEQ ID 2).

The present invention also provides a pair of oligonucleotides for the amplification of *M. leprae* derived EF-Tu sequences. This pair consists of an oligonucleotide comprising at least 10 consecutive nucleotides of the sequence as. depicted in SEQ ID 3 and an oligonucleotide comprising at least 10 consecutive nucleotides of the sequence as depicted in SEQ ID 4 respectively.

Again, for use in transcription based methods, one of the oligonucleotides may be linked to a promoter sequence, and an oligonucleotide provided with the T7 promoter sequence is depicted in SEQ ID 10. In the experimental part of the application such a pair is referred to as TUF 20 (SEQ ID 10) and TUF 22 (SEQ ID 4).

The present invention further provides a pair of oligonucleotides that are suitable for the amplification of *E. coli* derived EF-Tu sequences.

This pair consists of an oligonucleotide comprising at least 10 consecutive nucleotides of the sequence. as depicted in SEQ ID 5 and an oligonucleotide comprising at least 10 consecutive nucleotides of the sequence as depicted in SEQ ID 6 respectively.

Again, for use in transcription based methods, one of the oligonucleotides may be linked to a promoter sequence, and an oligonucleotide provided with. the T7 promoter sequence is depicted in SEQ ID 11. In the experimental part of the application such a pair is referred to as TUF 27 (SEQ ID. 11) and TUF 27 (SEQ ID 6).

These oligonucleotides are thus especially useful in the assessment of the viability of *M.tuberculosis, M.Leprae* or *E.coli.*

It is understood that oligonucleotides consisting of the sequences of the present invention may contain minor deletions, additions and/or substitutions of nucleic acid bases, to the extent that such alterations do not negatively affect the yield or product obtained to a significant degree. Where oligonucleotides according to the present invention are used as probes, the alterations should not result in lowering the hybridization efficiency of the probe.

For example, in case of transcription based amplification techniques, wherein one or more of the primers may be provided with a promoter sequence, the introduction of a purine-rich (=G or A) hybridizing sequence, just after the promoter sequence may have positive effects on the transcription (when there are C's and T's abortive transcription may occur). If no such sequence is available in the target nucleic acid a purine-rich sequence can be inserted in the oligonucleotide just following the last three G residues of the promoter sequence.

The sequences of the present invention are reflected as DNA sequences. The RNA equivalents of these sequences are likewise part of the present invention.

Part of the oligonucleotides according to the invention are particularly suitable for use as a probe in the detection of nucleic acid amplified with a pair of oligonucleotides according to the invention. When used as a probe, said oligonucleotides may be provided with a detectable label. Various labeling moieties are known in the art. Said moiety may, for example, either be a radioactive compound, a detectable enzyme (e.g. horse radish peroxidase (HRP)), a hapten like biotin, or any other moiety capable of generating a detectable signal such as a calorimetric, fluorescent, chemiluminescent or electrochemiluminescent signal.

Hybrids between oligonucleotides according to the invention and (amplified) target nucleic acid may also be detected by other methods known to those skilled in the art. Oligonucleotides according to the invention that are especially suitable as a probe for the detection of Mycobacterial Ef-Tu sequences consist essentially of the sequences as depicted in SEQ ID 7 and 8 (In the experimental part said sequences are depicted as TUF 25 and TUF 26 respectively.).

Together these probes can be used in a sandwich hybridization assay, whereby one can be used as capture probe and the other can be labeled with a detectable label.

A test kit for the detection of Mycobacterial EF-Tu mRNA in a sample is likewise part of the present invention. Such a kit may comprise

- a pair of oligonucleotides according to the invention and at least one oligonucleotide comprising a nucleic acid sequence substantially complementary to at least part of the amplified nucleic acid sequence, provided with a detectable label, as well as suitable amplification reagents.

These reagents are for example the suitable enzymes for carrying out the amplification reaction. A kit, adapted for use with NASBA for example, may contain suitable amounts of reverse transcriptase, RNase H and T7 RNA polymerase. Said enzymes may be present in the kit in a buffered solution but can likewise be provided as a lyophilized composition, for example, a lyophilized spherical particle. Such lyophilized particles have been disclosed in PCT appl. no. WO95/27721. The kit may further be furnished with buffer compositions, suitable for carrying out an amplification reaction. Said buffers may be optimized for the particular amplification technique for which the kit is intended as well as for use with the particular oligonucleotides that are provided with the kit. In transcription based amplification techniques, such as NASBA, said buffers may contain, for example, DMSO, which enhances the amplification reaction (as is disclosed in PCT appl. no. WO 91/02818).

Furthermore the kit may be provided with an internal control as a check on the amplification procedure and to prevent the occurrence of false negative test results due to failures in the amplification procedure. The use of internal controls in transcription based amplification techniques is described in PCT appl. no. WO 94/04706. An optimal control sequence is selected in such a way that it will not compete with the target nucleic acid in the amplification reaction. Kits may also contain reagents for the isolation of nucleic acid from biological specimen prior to amplification. A suitable method for the isolation of nucleic acid is disclosed in EP389063.

BRIEF DESCRIPTION OF THE FIGURES

FIG. 1*a:* The analytical sensitivity of NASBA using in vitro produced mycobacterial EF-Tu RNA.

FIG. 1*b:* The analytical sensitivity of NASBA using in vitro produced mycobacterial EF-Tu RNA.

FIG. 2: Specificity of the *M. tuberculosis* NASBA.

FIG. 3: Specificity of the *M. leprae* NASBA.

FIG. 4: NASBA for viability assessment.

EXAMPLES

Example 1

Selection of primers and probes for the amplification of EF-Tu mRNA of *M. tuberculosis, M. leprae* and *E. coli:*

Sources of RNA. Table 1 shows the sources of RNAs that were used in the experiments described in this and the following examples. The cultivable mycobacteria were grown on Löwenstein-Jensen slants for 2–3 weeks. *M. leprae* was isolated from spleen tissue of an experimentally infected armadillo (Dasypus novemcinctus Linn.), as recommended by the World Health Organization [WHO Expert Committee on Leprosy. (1988) Sixth Report Tech. Rep. Ser. 8. 768. World Health Organization, Geneva.]. Other bacteria which might be found in human and/or animal samples or which are closely related to mycobacteria (see Table 1), were used for controls. For Actinomyces israelii lyophilized bacteria were used. The strains used for the production of in vitro RNA are described below.

TABLE 1

Sources of RNA and specificity of NASBA

| | Species | Strain/source | Origin | ECL signal *M. tuberculosis* primers | | ECL signal *M. leprae* primers | |
|---|---|---|---|---|---|---|---|
| 1. | *Mycobacterium africanum* | myc 5544 | RIVM | 20810 | + | 2065 | – |
| 2. | *Mycobacterium avium* | 3875 (serovar 2) | RIVM | 1523<br>1344 | – | 1031<br>1217 | – |
| 3. | *Mycobacterium bovis* | 8316 | RIVM | 1E+08<br>2109782 | + | 970<br>1006 | – |
| 4. | *Mycobacterium bovis* | ATCC 19210 | RIVM | 36497<br>246050 | + | 1964 | – |
| 5. | *Mycobacterium bovis* BCG | ATCC 35733 | SSI | 117186<br>472834 | + | 1089<br>1069 | – |
| 6. | *Mycobacterium intracellulare* | IWGMT3 (serovar4) | RIVM | 1322<br>1310 | – | 920<br>1052 | – |
| 7. | *Mycobacterium kansasii* | 1012 | RIVM | 1418<br>1341 | – | 1060<br>1135 | – |
| 8. | *Mycobacterium leprae* | Armadillo isolate | KIT | 1001<br>3592 | – | 1543836<br>1E+08 | + |
| 9. | *Mycobacterium paratuberculosis* | 138601-24 | CDI | 1146<br>1125 | – | 851<br>1019 | – |
| 10. | *Mycobacterium scrofulaceum* | 3442 | RIVM | 1143<br>1167 | – | 870<br>1097 | – |
| 11. | *Mycobacterium smegmatis* | ATCC 14468 | RIVM | 1365<br>1289 | – | 954<br>1058 | – |
| 12. | *Mycobacterium tuberculosis* | 4514 | RIVM | 401796<br>24398 | + | 902<br>1914 | – |
| 13. | *Mycobacterium tuberculosis* | H37RV | RIVM | 144963 | + | 2051 | – |
| 14. | *Mycobacterium tuberculosis* | M. tub 193 | KIT | 1417077 | + | 501 | – |
| 15. | *Actinomyces israelii* | 103.62 | CBS | 886<br>1104 | – | 972<br>1974 | – |
| 16. | *Corynebacterium belfanti* | Clinical isolate | AMC | 1048<br>1029 | – | 966<br>1818 | – |
| 17. | Corynebacterium J. K. | Clinical isolate | AMC | 1108<br>1113 | – | 966<br>2082 | – |
| 18. | *Eschericia coli* | Clinical isoiate | AMC | 1129<br>1062 | – | 884<br>2219 | – |
| 18a. | *Eschericia coli* | INVaF' | Invitrogen (K2000-01) | NT | | NT | |
| 19. | *Haemophilus influenza* | Clinical isolate | AMC | 1097<br>1113 | – | 1042<br>2085 | – |
| 20. | *Klebsiella pneumoniae* | Clinical isolate | AMC | 1137<br>1117 | – | 1022<br>1957 | – |
| 21. | *Legionella pneumophila* | Clinical isolate | AMC | 1017<br>954 | – | 999<br>1914 | – |
| 22. | Nocardia asteroides | Clinical isolate | AMC | 970<br>1037 | – | 1239<br>2079 | – |
| 23. | *Pseudomonas aeruginosa* | Clinical isolate | AMC | 981<br>937 | – | 965<br>1757 | – |
| 24. | *Staphylococcus aureus* | Clinical isolate | AMC | 932<br>1006 | – | 967<br>2214 | – |
| 25. | *Streptococcus pneumoniae* | Clinical isolate | AMC | 909<br>985 | – | 977<br>2081 | – |
| 26. | *Homo sapiens* | Placenta | AMC | 1041 | – | 2073 | – |
| 27. | *Homo sapiens* | Placenta<br>Lot no. BD 41091901 | Pharmacia | 991 | – | 1986 | – |
| 28. | In Vitro RNA 1054<br>*Mycobacterium tuberculosis*<br>H37RV | 764 bp in PCR-II vector<br>pTHT 1054 (plasmid)<br>S1418 (strain INVaF') | KIT | 409019<br>1E+08 | + | 2088<br>809 | – |
| 29. | In Vitro RNA 1055<br>*Mycobacterium leprae*<br>Armadillo isolate | 764 bp in PCR-II vector<br>pTHT 1055 (plasmid)<br>S1419 (strain INVaF') | KIT | 992<br>764 | – | 1431525<br>624966 | + |
| 30. | In Vitro RNA 1057<br>*Eschericia coli*<br>Clinical isolate | 764 bp in PCR-II vector<br>pTHT 1057 (plasmid)<br>S1420 (strain INVaF') | KIT | 986<br>984 | – | 1896<br>776 | – |
| 31. | Water purified according to Boom et al. 1991 [9] | | Baker | 1194<br>960 | – | 1136<br>2062 | – |

TABLE 1-continued

Sources of RNA and specificity of NASBA

| | Species | Strain/source | Origin | ECL signal M. tuberculosis primers | | ECL signal M. leprae primers | |
|---|---|---|---|---|---|---|---|
| 32. | Water | | Baker | 995<br>678 | – | 2256<br>612 | – |

AMC = Academic Medical Centre, Amsterdam, The Netherlands; CBS = Netherlands Culture Collections of Micro-Organisms, Baarn, The Netherlands; CDI = Central Veterinary Institute, Lelystad, The Netherlands; KIT = Royal Tropical Institute, Amsterdam, The Netherlands; RIVM = National Institute of Public Health and Environment, Bilthoven, The Netherlands; SSI = Statens Serum Institute, Copenhagen, Denmark; ATCC = American Type Culture Collection, Rockville, USA.

Nucleic acid (NA) isolation. To perform the experiments described in all examples nucleic adds were isolated as we described previously [Vliet, G. M. E. van der, Schepers, P., Schukkink, R. A. F., Gemen, B. van and Klatser, P. R. (1994) Assessment of mycobacterial viability by RNA amplification. Antimicrob. Agents Chemother. 38, 1959–1965.]. In summary, all bacterial strains were adjusted to the turbidity equivalent of no. 4 McFarland barium sulphate nephelometer standard as described earlier [Verstijnen, C. P. H. J., H. M. Ly, K. Polman, C. Richter, S. P. Smits, S. Y. Maselle, P. Peerbooms, D. Rienthong, N. Montreewasuwat, S. Koanjanart, D. D. Trach, S. Kuijper, and A. H. J. Kolk (1991) Enzyme-linked immunosorbent assay using monoclonal antibodies for identification of mycobacteria from early cultures. J. Clin. Microbiol. 29, 1372–1375.]. Fifty μl of the diluted samples contained approximately $10^5$ viable mycobacteria as determined by counting the number of colony-forming units (not done for *M. leprae*). This volume was used for lysis and NA-isolation according to “protocol Y/SC” described by Boom et al. (1990) [Boom, R., C. J. A. Sol, M. M. M. Salimans, C. L. Jansen, P. M. E. Wertheim-Van Dillen and J. Van der Noordaa (1990). Rapid and simple method for purification of nucleic acids. J. Clin. Microbiol. 28, 495–503.]. The NA were eluted from the silica with 50 μl or 100 μl RNAse-free $H_2O$ and stored at −20° C.

Human placental NA were isolated in a similar fashion (kindly provided by Dr. H. Smits, Department of Virology, Academic Medical Hospital, Amsterdam, The Netherlands). Two μl containing 270 ng NA was tested. This amount corresponds to approximately $4\times10^5$ diploid human cells. Another batch of human NA was obtained commercially from Pharmacia (Uppsala, Sweden).

Example 2

Sensitivity and specificity of NASBA in the amplification of EF-Tu mRNA of *M.tuberculosis, M.leprae* and *E.coli:*

Selection of primers and probes. The primers and probes used in this study are listed in Table 2.

TABLE 2

Primers and probes

| Primer/ probe | Origin | Position | Sequence (5'-3') |
|---|---|---|---|
| TUF 4 | MTTUF | 1302–1284 | GTR CGG AAG TAG AAC TGC G |
| TUF 7 | MTTUF | 539–560 | GAC IIC CCI GGI CAC GCC GAC T |
| TUF 3F | MTTUF | 917–936 | Fluorescein-GAC AAG CCG TTC CTG MTG CC |
| TUF 4F | MTTUF | 1302–1284 | Fluorescein-GTR CGG AAG TAG AAC TGC G |
| TUF 8F | MTTUF | 936–917 | Fluorescein-GGC AKC AGG AAC GGC TTG TC |
| TUF 15 | MTTUF | 1057–1039 | aat tct aat acg act cac tat agg gAG AGC TTG GTC GTC GAT GGG CGA |
| TUF 18 | MTTUF | 855–875 | CCT CTG TCG AGG AAC TGA TGA |
| TUF 20 | MLTUF | 977–958 | aat tct aat acg act cac tat agg gAG AGG GTC GTC TGA CGA ATG CCG A |
| TUF 22 | MLTUF | 781–801 | AGT CTG TCA CAC AGT TGA TGG |
| TUF 24 | MLTUF<br>MTTUF | 862–843<br>936–917 | Digoxigenin-GGC ATC AGG AAC GGC TTG TC |
| TUF 25 | MLTUF<br>MTTUF | 920–937<br>994–1011 | Biotin-GCG CGG CGT GGT CAA CGT@ |
| TUF 26 | MLTUF<br>MTTUF | 940–957<br>1014–1031 | Ruthenium-ACG AGG AAG TTG AGA TCG |
| TUF 27 | ECTUF | 756–737 | aat tct aat acg act cac tat agg gAG AGC TGA GTC TCT TTG ATA CCA A |
| TUF 28 | ECTUF | 560–580 | CGA AAA TCC TGG AAC TGG CTG |
| TUF 29 | ECTUF | 699–716 | Biotin-ACG CGG TAT CAT CAA AGT |
| TUF 30 | ECTUF | 719–736 | Ruthenium-GTG AAG AAG TTG AAA TCG |

Abbreviations:
ECTUF = *E. coli* EF-Tu gene sequence (GenBank accession number J01717)
MTTUF = *M. tuberculosis* EF-Tu gene sequence (GenBank accession number X63539)
MLTUF = *M. leprae* EF-Tu gene sequence (GenBank accession number D13869)
I = Inosine, M = [A, C], K = [G, T], R = [A, G]
@The sequence shown is homologous to MLTUF and not to MTTUF (where the underlined G is an A).
TUF 15, 20 and 27 include the T7 promoter sequence which is shown in lower case.
The promoter sequence is followed by a purine rich region (AGAG) which is shown in italics.

The published nucleotide sequences of the EF-Tu genes of *M. tuberculosis* (GenBank accession number X63539), *M. leprae* (GenBank accession number D13869), *E. coli* (GenBank accession number J01717), *Micrococcus luteus* (GenBank accession number M17788) and *Streptomyces coelicolor* (GenBank accession number X77039) were aligned using the software programme GCG (National Institute of Health, USA)) installed on appropriate hardware. Degenerative primers TUF4 and TUF7 (Table 2) were selected to amplify a 764 bp DNA fragment of the EF-Tu genes by PCR from all organisms listed in Table 1. PCR was performed using 75 mM Tris-HCl, pH9.0, 20 mM $(NH_4)_2SO_4$, 0.01% (v/v): Tween 20, 4 mM $MgCl_2$, 0.2 mM of each dNTP, 125 ng of each primer and 1 U/reaction of Goldstar™ DNA polymerase (Eurogentec, Belgium). PCR was initiated by incubation at 94° C. for 3 min followed by 35 cycles of 1.15 min at 94° C., 1 min at 55° C. and 2 min at 72° C. The generated PCR fragments of the DNA of the organisms listed in Table 1, except *C.belfanti, H.influenza, S.aureus, S.pneumoniae* and *H.sapiens* were purified using a MicroSpin™ Sephacryl™ 300 HR column (Pharmacia) to remove excess of primers. The purified fragments were sequenced directly using primers TUF 3F, 4F and 8F by applying the Autocycle Sequencing Kit (Pharmacia) and the A.L.F. automatic DNA sequencer (Pharmacia). Sequences were edited by using the DNASIS™ software programme (Pharmacia) and clustal alignments were then made using the PCGene software programme.

Selection of primers and probes. Table 3 shows the seven variable regions of the EF-Tu sequences which were defined based on the clustal alignments. From these variable regions it is possible to select primers and probes enabling species-specific detection of EF-Tu mRNA of different organisms (Table 4).

Table 5 shows the clustal alignments of two (region IV and VI) of the seven variable regions of the EF-Tu sequence on the basis of which the primers and probes were selected for specific amplification of *M.tuberculosis, M.leprae* and *E.coli* EF-Tu mRNA through NASBA The criteria to select these two areas were: the availability of species-specific primers, a genus-specific probe and a length of ±200 nucleotides of the fragment to be amplified.

TABLE 3

Seven variable regions on the EF-Tu sequences

| Variable Region | Position on the EF-Tu sequence (in bp) of Mycobacterium tuberculosis AC X63539 |
|---|---|
| I. | 673–703 |
| II. | 774–793 |
| III. | 820–823 |
| IV. | 852–871 |
| V. | 955–970 |
| VI. | 1039–1051 |
| VII. | 1123–1142 |

TABLE 4

Parts of the EF-Tu mRNA variable sequences which can be used for the selection of primers and/or probes enabling species-specific detection of EF-Tu mRNA from different organisms.

| Region | Sequence | Specific for |
|---|---|---|
| I. | AGTGGGTGTGCCCTACATCCTGGTAGCGCTG | *Mycobacterium tuberculosis* complex |
| | GGTGGGTGTACCTTACATCCTGGTCGCACTT | *Mycobacterium leprae* |
| | GGTCGGTGTGCCCTACATCCTGGTCGCGCTG | *Mycobacterium avium* and *Mycobacterium paratuberculosis* |
| | GGTCGGCGTGCCCGCCCTGCTCGTGGCCCTG | *Micrococcus luteus* |
| | GGTCGGCGTTCCGTACATCGTGGTCGCCCTG | Streptomyces coelicolor |
| | GGTTGGCGTTCCTTACATCCTCGTTGCTCTT | *Corynebacterium glutamicum* |
| | GGTTGGCGTTCCTTACATCCTGGTTGCACTG | Corynebacterium J. K. |
| | GGTAGGCGTTCCGTACATCATCGTGTTCCTG | *Eschericia coli*, Nocardia asteroïdes and *Klebsiella pneumoniae* |
| | GGTAGGCGTTCCCTACATCGTCGTGTTCCTG | *Pseudomonas aeruginosa* |
| II. | CTGCCCAGGAATTCGACGAG | *Mycobacterium tuberculosis* complex and *Mycobacterium leprae* |
| | CCGCCCAGGAGTTCGACGAG | *Mycobacterium avium* and *Mycobacterium paratuberculosis* |
| | CCGCCCAGGAGTTC | *Mycobacterium intracellulare* |
| | TCTCAGTACGACTTCCCGGGC | *Eschericia coli* |
| | TCTCAGTACGATTTCCCGGGC | Nocardia asteroïdes and *Klebsiella pneumoniae* |
| | CCTCCAGGAGCTTCGACGTC | *Micrococcus luteus* |
| | CTCCGAGTACGAGTTCCCGGGCGAC | Streptomyces coelicolor |
| | CTGAGCAGGACTACGAC | *Corynebacterium glutamicum* |
| | AACACCTACGACTTCCCGGGC | *Pseudomonas aeruginosa* |
| III. | GCTC | *Mycobacterium tuberculosis* complex, *Mycobacterium avium*, *Mycobacterium paratuberculosis* and *Mycobacterium intracellulare* |
| | ATTG | *Mycobacterium leprae* |
| | TCTG | *Micrococcus luteus*, Streptomyces coelicolor, *Corynebacterium glutamicum*, *Eschericia coli*, Nocardia asteroïdes, *Klebsiella pneumoniae* and *Actinomyces israelii* |
| | GCTG | *Pseudomonas aeruginosa* |
| IV. | TTGCTCTGTCGAGGAACTGATGA | *Mycobacterium tuberculosis* complex |
| | TTGCCTCTGTCGAGGAACTGATGA | *Mycobacterium tuberculosis* (AC X63539) |
| | TCGAGTCTGTCACACAGTTGATGG | *Mycobacterium leprae* |
| | TCAAGTCCGTCGAGGACCTCATGG | *Micrococcus luteus* |
| | GCAACTCGGTCCTCGAGCTCATGA | Streptomyces coelicolor |
| | GCAAGCAGATCCTTGAGCTCATGC | *Corynebacterium glutamicum* |

TABLE 4-continued

Parts of the EF-Tu mRNA variable sequences which can be used for the selection of primers and/or probes enabling species-specific detection of EF-Tu mRNA from different organisms.

| Region | Sequence | Specific for |
| --- | --- | --- |
| | TGGAGTCCGTCGAGCAG | *Mycobacterium avium* and *Mycobacterium paratuberculosis* |
| | AAGCGAAAATCCTGGAACTGGCTGGC | *Eschericia coli* |
| | AAGCGAAAATC | Nocardia asteroïdes and *Klebsiella pneumoniae* |
| V. | CATTACCGGCCGCGGA | *Mycobacterium tuberculosis* |
| | TATCACCGGTCGTGGC | *Mycobacterium leprae* |
| VI. | TCGGCATTCGCCCATCGACCACCAAG | *Mycobacterium tuberculosis* complex |
| | TCGGCATTCGTCAGACGACCACCAAG | *Mycobacterium leprae* |
| | TCGGCATCCGCCCGACCAGCACCAAG | *Mycobacterium intracellulare* |
| | TCGGCATCCGCCCGTCCAGCACCAAG | *Mycobacterium avium* and *Mycobacterium paratubercuiosis* |
| | TCGGCATCCGCCCGGAGACCACCAAG | *Mycobacterium smegmatis* |
| | TTGGTATCAAAGAGACTCAGAAGT | *Eschericia coli* |
| | TTGGTATCAAAGAGACCGCGAAAA | *Klebsiella pneumoniae* |
| | TCGGCATCAAGGCGACCACCAAGA | *Pseudomonas aeruginosa* |
| | CATTAAGCCGCCCAGCACCAAGA | *Mycobacterium scrofulaceum* |
| | TCGGCATCCGTCCGACACCACCAAGA | *Mycobacterium kansasii* |
| VII. | TGGTTTGCTGCTGCGGGGCG | *Mycobacterium tuberculosis* complex |
| | TGGTCTGTTGTTGCGTGGCA | *Mycobacterium leprae* |
| | CGGTCTGCTGCTGCGTGGTA | *Mycobacterium intracellulare*, *Mycobacterium avium* and *Mycobacterium paratuberculosis* |
| | TGGTAACCTGCTGCGCTGGCA | *Pseudomonas aeruginosa* |
| | CGGTCTGTTGCTCCGTGGCA | *Mycobacterium scrofulaceum* |
| | CGGGTCTGTTTGCTGCGTGGTG | *Mycobacterium kansasii* |
| | AGGTGTTCTGCTGCGCGGTA | *Eschericia coli* |
| | AGGTGTTCTGCTGCGTGGTA | *Klebsiella pneumoniae* |

TABLE 5

Two clustal alignments (region IV and VI) of the variable regions of the EF-Tu sequence

| Species | Number AC or Table 1 | Sequence (Region IV) |
| --- | --- | --- |
| *Mycobacterium tuberculosis* | X63539 | TTGCCTCTGTC--GAGGAA--CT-GATGA |
| *Mycobacterium leprae* | D13869 | TCGAGTCTGTC--ACACAG--TT-GATGG |
| *Micrococcus luteus* | M17788 | TCAA----GTCCGTCGAGGACCT-CATGG |
| Streptomyces coelicolor | X77039 | GCAACTCGGTCC-TCGAG---CT-CATGA |
| *Corynebacterium glutamicum* | X77034 | GCAAG-CAGATC--CTTGAGC-T-CATGC |
| *Mycobacterium leprae* | 8 | TCGAGTCTGTCA--AC |
| *Mycobacterium tuberculosis* H37Rv | 13 | TTG---C--TCTGTCGAGGAACT-GAT |
| *Mycobacterium bovis* | 3,4 | TTG---C--TCTGTCGAGGAACT-GAT |
| *Mycobacterium bovis* BCG | 5 | TTG---C--TCTGTCGAGGAACT-GAT |
| *Mycobacterium avium* | 2 | TGG---A-GTCCGTCGAGCAGCT-GAT |
| *Mycobacterium paratuberculosis* | 9 | TGG---A-GTCCGTCGAGCAG |
| *Mycobacterium tuberculosis* | 12 | TTG---C--TCTGTCGAGG |
| *Eschericia coli* | JO1717 | AAGCGAAAATC---CTGGAACTGGCTGGC |
| *Eschericia coli* | 18 | AAGCGAAAATC---CTGGAACTG |
| *Nocardia asteroïdes* | 22 | AAGCGAAAATC |
| *Mycobacterium leprae* | D13869 | TCGGCATTCGTCAGA-CGACCACCAAG |
| *Mycobacterium tuberculosis* | X63539 | TCGGCATTCGCCCAT-CGACCACCAAG |
| *Mycobacterium bovis* | 4 | TCGGCATTCGCCCAT-CGACCACCAAG |
| *Mycobacterium leprae* | 8 | TCGGCATTCGTCAGA-CGACCACCAAG |
| *Mycobacterium intracellulare* | 6 | TCGGCATCCGCCCGA-CCAGCACCAAG |
| *Mycobacterium bovis* BCG | 5 | TCGGCATTCGCCCAT-CGACCACCAAG |
| *Mycobacterium tuberculosis* | 12 | TCGGCATTCGCCCAT-CGACCACCAAG |
| *Mycobacterium tuberculosis* H37Rv | 13 | TCGGCATTCGCCCAT-CGACCACCAAG |
| *Mycobacterium avium* | 2 | TCGGCATCCGCCCGT-CCAGCACCAAG |
| *Mycobacterium paratuberculosis* | 9 | TCGGCATCCGCCCGT-CCAGCACCAAG |
| *Mycobacterium smegmatis* | 11 | TCGGCATCCGCCCGGA-GACCACCAAG |
| *Mycobacterium scrofulaceum* | 10 | TCAGCATTAAGCCGC-CCAGCACCAAG |
| *Mycobacterium kansasii* | 7 | TCGGCATCCGTCCGA-CACCACC-MG |
| *Eschericia coli* | 18 | TTGGTAT----CAAAGAGA-CTCAGAAGT |
| *Klebsiella pneumoniae* | 20 | TTGGTAT----CAAAGAGA-CCGCGAAAA |
| 9*Pseudomonas aeruginosa* | 23 | TCGGCAT----CAAGGCGA-CCACCAAGA |

Based on these alignments species-specific primers for the use in NASBA were selected for *M.tuberculosis* (TUF 15 and 18), for *M.leprae* (TUF 20 and 22) and for *E.coli* (TUF 27 and 28). A generic capture probe TUF 25 and detection probe TUF 26 were chosen for the detection of the mycobacterial RNA amplicons by electrochemiluminescence (ECL). Probe TUF 25 is homologous to the EF-Tu sequence of *M.leprae* and not to that of *M.tuberculosis;* the difference is one nucleotide (G→A; see Table 2). However, this difference did not affect the detection of amplicons generated from RNA originating from *M.tuberculosis*. For the detection of *E.coli* RNA amplicons we used the specific capture and detection probes TUF 29 and TUF 30, respectively.

In region IV one nucleotide difference was found with the published sequence of EF-Tu of *M.tuberculosis* [GenBank accession number X63539]: in none of the strains belonging to the *M.tuberculosis* complex a C at position 855 was found. However, the primer position was chosen in such a way that this discrepancy would not influence the amplification reaction.

Example 3

Specificity and Sensitivity Testing of *E.coli* by Amplification of EF-Tu mRNA

Isolation of in vitro RNA.

A 764 bp fragment of the EF-Tu gene of *M. tuberculosis* H37Rv, *M. leprae* and *E. coli* (Table 1) was amplified via PCR using the primer set TUF 4 and TUF 7 (Table 2), as described above. The amplified product was cloned into the pCR II vector using the TA-cloning kit (Invitrogen) following the manufacture's instructions. Selection of the appropriate clone with the insert in the correct orientation, size and specificity was determined by restriction enzyme analysis and PCR.

After linearization of the plasmid with the restriction enzymes Bam HI and Hind III, the cloned insert within the polylinker region was transcribed from the T7 promoter site using the SP6/T7 transcription kit (Boehringer, Mannheim). The DNA template was removed by digestion with RQI DNAse (Promega) and the RNA was purified by the RNeasy kit from Qiagen according the manufacturer's protocol. Purity was checked by agarose gel electrophoresis and Northern blotting with digoxigenine-labelled probe TUF 24 according to standard procedures. The in vitro RNA was quantified by measuring the extinction at 260 nm.

RNA Amplification

A 203, 197 and 198 nucleotide fragment of the EF-Tu mRNA of *M.tuberculosis, M.leprae* and *E.coli,* respectively, was amplified by the NASBA technique essentially as described before [Vliet, G. M. E. van der, Schepers, P., Schukkink, R. A. F., Gemen, B. van and Klatser, P. R. (1994) Assessment of mycobacterial viability by RNA amplification. Antimicrob. Agents Chemother. 38, 1959–1965.]. The 20 $\mu$l reaction mix was composed of 40 mM Tris-HCl, pH 8.5, 12 mM $MgCl_2$, 70 mM KCl, 5 mM DTT, 1.5 M sorbitol, 2.1 mg BSA, 1 mM of each dNTP, 2 mM of ATP, CTP, UTP, 1.5 mM of GTP and 0.5 mM ITP, 15% (v/v) DMSO, 0.2 mM Primer 1 and Primer 2, 0.08 U RNase H, 32 U T7 RNA polymerase, 6.4 U AMV-RT polymerase and the RNA target. Isothermal amplification of the RNA target was performed by incubation of these samples at 41° C. for 2.0 h.

Detection of the amplified RNA was done by in-solution hybridization in the ECL detection assay, as described previously [Gemen, B. van, Beuningen, R van, Nabbe, A., Strip. D. van, Jurriaans, S., Lens, P., Kievits, T. (1994) A one tube quantitative HIV-I RNA NASBA nucleic acid amplification assay using electrochemiluminescent (ECL) labelled probes. J. Virol. Methods, 49, 1] with minor modifications: 5 $\mu$l of NASBA amplified RNA was either diluted 20-fold in RNase-free water or used undiluted. A 5'-biotinylated probe was used to capture the NASBA product. The detection probe used was tris [2,2-bipyridine] ruthenium [II] complex labelled. This label emits light as a result of chemical reactions taking place at the surface of an electrode. The cutoff value was set at 3000. The ECL detection assay was measured on a scale of 0 to $10^8$.

Controls for Amplification

Negative controls (water only) were included in each experiment in order to check for carry-over contamination during NA-extraction and amplification. These control samples were extracted and amplified by NASBA in the same manner as described above.

Sensitivity and Specificity of the Mycobacteria NASBA

For determination of the sensitivity of the NASBA, *M.tuberculosis* ATCC 35801 was grown in liquid Tween™ Albumin medium at 37° C. The concentration at the start of the culture was $8.10^6$ bacteria/ml. Growth of the bacteria was monitored by measuring the extinction at 420 nm. After 13 days of culture a sample was taken and diluted in lysis buffer [Boom, R., C. J. A. Sol, M. M. M. Salimans, C. L. Jansen, P. M. E. Wertheim-Van Dillen and J. Van der Noordaa (1990). Rapid and simple method for purification of nucleic adds. J. Clin. Microbiol. 28, 495–503.]. Serial dilutions were made in lysis buffer, RNA purified [Boom, R., C. J. A. Sol, M. M. M. Salimans, C. L. Jansen, P. M. E. Wertheim-Van Dillen and J. Van der Noordaa (1990). Rapid and simple method for purification of nucleic acids. J. Clin. Microbiol. 28, 495–503.] and each dilution was tested in NASBA to determine the highest dilution still giving a positive NASBA signal. In addition the analytical sensitivity of NASBA was determined using serial dilutions of in vitro RNA (see above). The specificity of NASBA was determined using the purified RNA from different organisms (Table 1, see above).

Sensitivity and Specificity of the *E.coli* NASBA.

*E.coli* was grown in Luria Broth (LB) liquid medium at 37° C. for 18 h. The suspension thus obtained was inoculated in fresh medium (1:200)(OD 600 nm=0.015) and incubated at 37° C. in a gyrotory shaker for 3 h and 15 min (OD 600 nm=0.430). A serial dilution was made and mRNA was purified as described above. In addition, the same dilutions were plated onto LB agar plates which were incubated at 37° C. for 18 h after which colonies were counted.

The analytical sensitivity of NASBA was determined using serial dilutions of in vitro RNA (see above).

Results

Sensitivity of NASBA. The analytical sensitivity of NASBA using in vitro produced EF-Tu RNA is illustrated in FIG. 1*a* and 1*b*. Both the *M.tuberculosis* NASBA and the *M.leprae* NASBA had a detection of 50 molecules of RNA (FIG. 1*a*). The detection limit of the *M.tuberculosis* NASBA when using bacteria as starting material for detection was 12,000 (result not shown).

The analytical sensitivity of the *E.coli* NASBA was shown to be 100 molecules (FIG. 1*b*). The detection limit of the *E.coli* NASBA when using bacteria as starting material for detection was 0.4 (result not shown).

Specificity of NASBA. The specificity of the *M.tuberculosis* NASBA and the *M.leprae* NASBA is illustrated in FIGS. 2 and 3, respectively.

The *M.tuberculosis* NASBA showed specificity for the RNA purified from bacteria belonging to the *M.tuberculosis* complex only. Furthermore, as illustrated in FIG. 2, the *M.tuberculosis* NASBA showed a positive reaction when homologous in vitro produced EF-Tu RNA was used as target.

The *M.leprae* NASBA showed specificity for *M.leprae* RNA only and its homologous in vitro produced RNA.

Example 4

Viability Testing of *E.coli*

*E.coli* was grown in LB liquid medium at 37 ° C. for 18 h. The suspension thus obtained was inoculated in fresh medium (1:100)(OD 600 nm=0.001) and incubated at 37° C. in a gyrotory shaker for 4 h. The suspension was then divided in two equal parts. To one part a cocktail of antibiotics was added to kill the bacteria: ampicillin, rifampicin and kanamycin (each 50 $\mu$g/ml); the other part was left untouched. Both were incubated at 37° C. for another 3 h and 30 min. Every 30 min the OD at 600 nm was monitored and a 100 sample from each culture was taken and added to 900 lysis buffer; mRNA was purified as described above). In addition, viability of the *E.coli* bacteria was monitored by overlaying a sample (100) onto LB agar plates. Colonies were counted after 18 h incubation at 37° C.

The NASBA signals increased and reached its maximum level when *E.coli* was left to grow untouched (FIG. 4). However, when antibiotics were added to the exponentially growing *E.coli* culture, the NASBA signal decreased 1 h after the addition of the antibiotics. This drop in mRNA concentration as measured by NASBA was coinciding with a decrease in the number of viable counts (FIG. 4).

---

We claim:

1. A method for assessing mycobacterial viability, comprising the steps of amplifying a target containing mRNA coding for the elongation factor EF-Tu, determining the presence and/or amount of said mRNA, and assessing mycobacterial viability based on the determination of the presence and/or amount of said mRNA.

2. The method according to claim 1, wherein said amplification reaction is a transcription based amplification reaction.

3. The method according to claim 2, wherein the transcription based amplification reaction is NASBA.

4. The method according to claim 1, wherein the amplified mRNA is detected with a complementary labeled probe.

5. The method according to claim 4, wherein the probe is provided with an electro-chemiluminescent label.

6. The method according to claim 1, wherein the Mycobacteriae species are *M. tuberculosis* or *M. leprae.*

7. A method for assessing the viability of *M. tuberculosis, M. leprae,* comprising the steps of amplifying EF-Tu mRNA with a pair of oligonucleotides selected from the group consisting of:

(a) an oligonucleotide comprising at least 10 consecutive nucleotides of the sequence according to SEQ ID NO:1 that hybridize with mRNA coding for the elongation factor EF-Tu and an oligonucleotide consisting of at least 10 consecutive nucleotides of SEQ ID NO:2 to assess the viability of *M. tuberculosis;*

(b) an oligonucleotide comprising at least 10 consecutive nucleotides of the sequence according to SEQ ID NO:3 that hybridize with mRNA coding for the elongation factor EF-Tu and an oligonucleotide consisting at least 10 consecutive nucleotides of SEQ ID NO:4 to assess the viability of *M. leprae;* and (c) an oligonucleotide comprising at least 10 consecutive nucleotides of the sequence according to SEQ ID NO:5 that hybridize with mRNA coding for the elongation factor EF-Tu and an oligonucleotide consisting of at least 10 consecutive nucleotides of SEQ ID NO:6 to assess the viability of *E. coli;* detecting the presence and/or amount of said mRNA; and assessing bacterial viability based on the detection of the presence and/or amount of said mRNA.

8. The method of claim 7, wherein said detection step is conducted using a sandwich hybridization assay and the viability of *M. tuberculosis* or *M. leprae* is assessed with a capture probe comprising at least 10 consecutive nucleotides of SEQ ID NO: 7 that hybridize with mRNA coding for the elongation factor EF-Tu and a labeled detection probe consisting of at least 10 consecutive nucleotides of SEQ ID NO: 8.

9. The method of claim 1, wherein said detection step is conducted using a sandwich hybridization assay and the viability of *E. coli* is assessed with a capture probe comprising at least 10 consecutive nucleotides of SEQ ID NO: 12 that hybridize with mRNA coding for the elongation factor EF-Tu and a labeled detection probe consisting of at least 10 consecutive nucleotides of SEQ ID NO 13.

* * * * *